US012623004B2

(12) United States Patent
Matsui

(10) Patent No.: US 12,623,004 B2
(45) Date of Patent: May 12, 2026

(54) SURFACE TREATMENT METHOD FOR SURGICAL IMPLANT AND SURGICAL IMPLANT

(71) Applicant: SUGINO MACHINE LIMITED, Namerikawa City (JP)

(72) Inventor: Taiki Matsui, Namerikawa City (JP)

(73) Assignee: SUGINO MACHINE LIMITED, Namerikawa City (JP)

( * ) Notice: Subject to any disclaimer, the term of this patent is extended or adjusted under 35 U.S.C. 154(b) by 278 days.

(21) Appl. No.: 18/402,646

(22) Filed: Jan. 2, 2024

(65) Prior Publication Data

US 2024/0226381 A1    Jul. 11, 2024

(30) Foreign Application Priority Data

Jan. 6, 2023    (JP) ................................. 2023-000956

(51) Int. Cl.
    *A61L 27/50*        (2006.01)
    *A61L 27/06*        (2006.01)
    (Continued)

(52) U.S. Cl.
    CPC .............. *A61L 27/50* (2013.01); *A61L 27/06* (2013.01); *A61L 2400/18* (2013.01);
    (Continued)

(58) Field of Classification Search
    CPC ...... A61L 27/50; A61L 27/06; A61L 2400/18;
    B22F 3/1146; B24C 1/10; B33Y 80/00
    See application file for complete search history.

(56) References Cited

U.S. PATENT DOCUMENTS

2017/0027624 A1*   2/2017   Wilson .................... B23K 26/08
2018/0333782 A1*  11/2018   Gallagher ............... A61L 27/04
                            (Continued)

FOREIGN PATENT DOCUMENTS

JP        2017-520282 A      7/2017
JP        2018-535811 A     12/2018

OTHER PUBLICATIONS

Sato, M. et al "Using Cavitation Peening to Improve the Fatigue Life of Titanium Alloy Ti—6Al—4V Manufactured by Electron Beam Melting" Materials Sciences and Applications 7, 181-191, Apr. 20, 2016. (Year: 2016).*

(Continued)

*Primary Examiner* — Anita K Alanko
(74) *Attorney, Agent, or Firm* — United IP Counselors, LLC

(57)    ABSTRACT

Provided is a surface treatment method for a surgical implant that improves fatigue strength of the surgical implant while maintaining the microscopic surface structure of the surgical implant. A surface treatment method for a surgical implant, including: placing an additive manufactured surgical implant in a processing liquid, the surgical implant including a microscopic surface structure having a complete penetration area and an incomplete penetration area; and causing a nozzle immersed in the processing liquid to eject a cavitation jet of the processing liquid to the surgical implant to remove the incomplete penetration area remaining on a surface of the surgical implant and apply a compressive residual stress to the surface of the surgical implant.

10 Claims, 7 Drawing Sheets

3b

(51) Int. Cl.
| | |
|---|---|
| *B22F 3/11* | (2006.01) |
| *B24C 1/10* | (2006.01) |
| *B33Y 80/00* | (2015.01) |

(52) U.S. Cl.
CPC .............. *B22F 3/1146* (2013.01); *B24C 1/10* (2013.01); *B33Y 80/00* (2014.12)

(56) References Cited

U.S. PATENT DOCUMENTS

| | | | |
|---|---|---|---|
| 2019/0271050 A1* | 9/2019 | Craft ........................ | C21D 7/06 |
| 2019/0388128 A1 | 12/2019 | Wilson et al. | |
| 2024/0424564 A1* | 12/2024 | Garcia ..................... | B24C 1/10 |

OTHER PUBLICATIONS

Hanawa, Biocompatibility of Titanium—favorable properties, Journal of The Japan Institute of Light Metals, vol. 62, No. 7 (2012), 285-290.

Office Action mailed on Oct. 31, 2023 in a corresponding Japanese Patent Application No. 2023-000956 (5 pages).

Soyama Hitoshi et al., "The use of various peening methods to improve the fatigue strength of titanium alloy Ti6Al4V manufactured by electron beam melting", Aims Materials Science, vol. 5, No. 5, Oct. 29, 2018 (Oct. 29, 2018), pp. 1000-1015, XP055960167, ISSN: 2372-0484, DOI: 10.3934/matersci.2018.5.1000.

Soyama Hitoshi et al., "A critical comparative review of cavitation peening and other surface peening methods", Journal of Materials Processing Technology, Elsevier, NL, vol. 305, Apr. 5, 2022 (Apr. 5, 2022), XP087040902, ISSN: 0924-0136, DOI: 10.1016/J. JMATPROTEC.2022.117586 [retrieved on Apr. 5, 2022].

He Peiyu et al., "Research on the water cavitation peening process and mechanism of TC4 titanium alloy", The International Journal of Advanced Manufacturing Technology , vol. 112, No. 5-6, Jan. 2, 2021(Jan. 2, 2021), pp. 1259-1269, XP0 37336674, ISSN :0268-3768, DOI :10.1007 / S00170-020-06566-2.

Extended European Search Report mailed on Jun. 12, 2024 in a corresponding European Patent Application No. 23218261.8 (8 pages).

* cited by examiner

SURFACE TREATMENT METHOD FOR SURGICAL IMPLANT AND SURGICAL IMPLANT

CROSS-REFERENCE TO RELATED APPLICATIONS

This application claims the benefit of priority to Japanese Patent Application No. 2023-000956, filed on Jan. 6, 2023, the entire contents of which are hereby incorporated by reference.

BACKGROUND

1. Technical Field

The present invention relates to a surface treatment method for surgical implant and a surgical implant.

2. Description of the Background

Incomplete penetration areas may remain on a surface of surgical implants produced by additive manufacturing. Surgical implants implanted in vivo may also be destroyed by fracture, work hardening, fatigue, and erosion (Hanawa, Biocompatibility of Titanium—favorable properties, Journal of The Japan Institute of Light Metals, Vol. 62, No. 7 (2012), 285-290).

BRIEF SUMMARY

A surgical implant preferably has a microscopic surface structure.

An object of the present invention is to provide a surface treatment method for a surgical implant that improves the fatigue strength of the surgical implant while maintaining the microscopic surface structure of the surgical implant.

A first aspect of the present invention provides a surface treatment method for a surgical implant, the method including:

placing an additive manufactured surgical implant in a processing liquid, the surgical implant including a microscopic surface structure having a complete penetration area and an incomplete penetration area; and causing a nozzle immersed in the processing liquid to eject a cavitation jet of the processing liquid to the surgical implant to remove the incomplete penetration area remaining on a surface of the surgical implant and apply a compressive residual stress to the surface of the surgical implant.

A second aspect of the present invention provides a surgical implant formed of pure titanium or titanium alloy, the surgical implant including:

an additive manufactured microscopic surface structure, wherein the surgical implant has a surface residual stress of negative value measured by X-ray stress measurement (cos α method).

The surgical implants are, for example, artificial bones, artificial joints, artificial vertebral bodies, or artificial intervertebral disc. The bioinert metal is, for example, pure titanium, a titanium alloy, a cobalt chromium alloy or stainless steel. The titanium alloy is, for example, a Ti-6Al-4V alloy, a Ti-6Al-7Nb alloy, or a Ti-15Mo-5Z4-3Al alloy.

The incomplete penetration area is formed on the surface of the surgical implant. The incomplete penetration area is formed of the same material as the surgical implant. The incomplete penetration area is, for example, a metal particle.

The incomplete penetration area is partially integral with the surgical implant. The incomplete penetration area includes manufacturing defects.

Within the microscopic spherical structure, a narrow base portion means that, for example, the diameter of the narrowest portion of the base portion is 70% or less than the diameter of the spherical portion.

The additive manufacturing methods are, for example, 3D printing, or additive manufacturing by thermal spraying. The surface of the surgical implants produced by additive manufacturing has a tensile residual stress.

The surgical implant is immersed in the processing liquid and the processing liquid is ejected from the nozzle immersed in the processing liquid. At this time, cavitation occurs due to a pressure difference around the jet of the processing liquid. The processing liquid is pure water or an aqueous solution containing a rust inhibitor. Examples of the rust inhibitor include amines and amine salts. In the cavitation processing, when the pressure becomes lower than the saturated vapor pressure for a very short time in the flow of the liquid, a large number of fine bubbles are generated by boiling of the liquid or liberation of the dissolved gas using the fine bubble nucleus as a nucleus. The bubbles collide with the surgical implant with the force of the jet. The bubbles repeatedly expand and contract to become smaller. The bubble is depressed to generate a micro jet flow, and the bubble is split and disappears. The micro jet flow erodes the surface of the surgical implant. It also imparts a compressive residual stress to the surface of the surgical implant. The cavitation removes the incomplete penetration area of the surgical implant. The jet containing bubbles generated by cavitation is referred to as a cavitation jet.

The surface treatment method for the surgical implant according to the present invention improves the fatigue strength of the surgical implant while maintaining the microscopic surface structure of the surgical implant.

DETAILED DESCRIPTION

Figure 1:
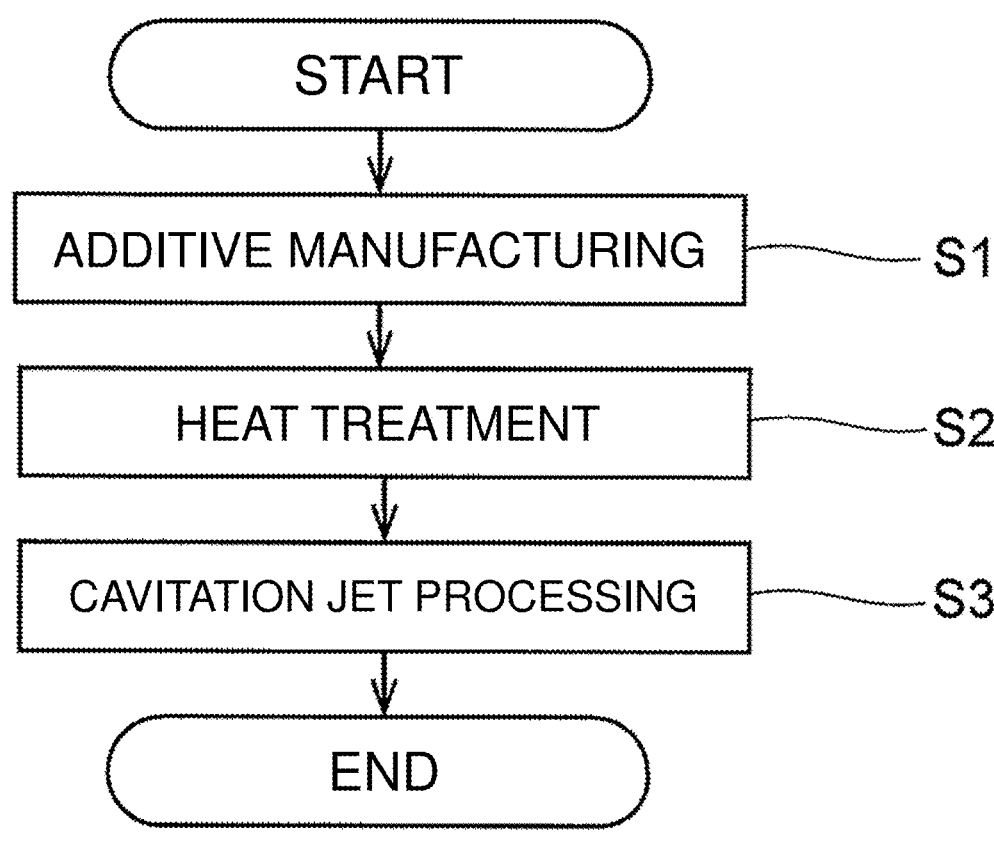
FIG. 1 is a flowchart showing a manufacturing method of a surgical implant according to an embodiment.

As shown in FIG. 1, in a manufacturing method of a surgical implant 3 according to a present embodiment, the surgical implant is firstly additive manufactured (step S1). The surgical implant is then heat treated (step S2). A cavitation jet processing is then performed to the surgical implant (step S3).

In step S1, an additive manufacturing is carried out by, for example, 3D printing, or thermal spraying. The 3D printing is, for example, a powder bed fusion (PBF). The additively manufactured surgical implants have tensile residual stresses.

The surgical implants have a microscopic surface structure. The surface structure has a large structure and a microstructure. The large structure has a size of the order of 0.1 mm to 1 mm. The large structures are regularly repeatedly arranged as shaped pattern. The microstructure has a size of the order of 1 μm to 10 μm. The microscopic surface structure is, for example, a microscopic spherical structure, a porous body structure, or a fiber structure. The microscopic surface structure appears randomly.

Figure 2:
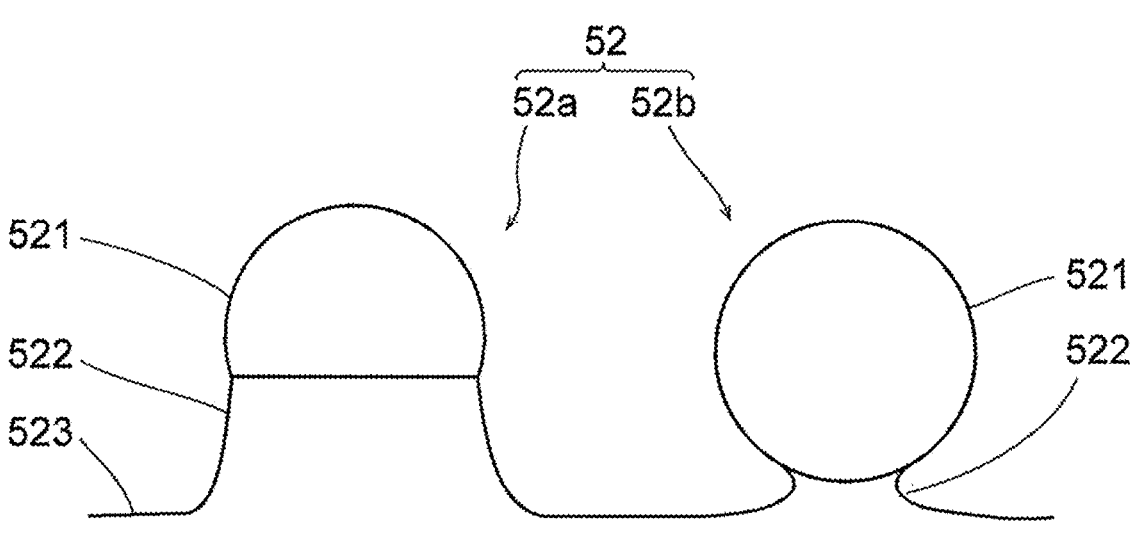
FIG. 2 is a schematic diagram showing a microscopic spherical structure of the surgical implant according to the embodiment.

As shown in FIG. 2, the surgical implant 3 manufactured by PBF has microscopic spherical structures 52. The microscopic spherical structure 52 is a structure in which the shape of the powder constituting the powder bed at the time of forming appears on the surface. The microscopic spherical structure 52 has a complete penetration area 52*a* and an incomplete penetration area 52*b*. The microscopic spherical structure 52 includes a spherical portion 521, a base portion 522, and a substrate 523. The base portion 522 of the complete penetration area 52*a* is wide. The base portion 522 of the complete penetration area 52*a* thus securely adheres to the substrate 523. The base portion 522 of the incomplete penetration area 52*b* is narrower than the base portion 522 of the complete penetration area 52*a*. The base portion 522 and the substrate 523 of the incomplete penetration area 52*b* are thus weakly connected to each other. The base portion 522 of the incomplete penetration area 52*b* has a narrowest part having a diameter that is approximately 70% or less than the diameter of the spherical portion 521.

In step S2, the surgical implants are heat treated by vacuum heat treatment or hot isostatic pressing (HIP).

The additively manufactured surgical implant 3 is treated by the vacuum heat treatment method to inhibit oxidation of the surface of the surgical implant and can be tempered, annealed, solutionized, and aged.

The additively manufactured surgical implant 3 is treated by the HIP method to remove residual cavities in the surgical implant 3. This densifies the surgical implant 3. The HIP method can also apply residual stresses to the surgical implants 3. For example, a residual stress (tensile stress) of 5 MPa to 20 MPa is applied to the titanium-based surgical implant 3.

Note that the step S2 may be omitted.

Figure 3:
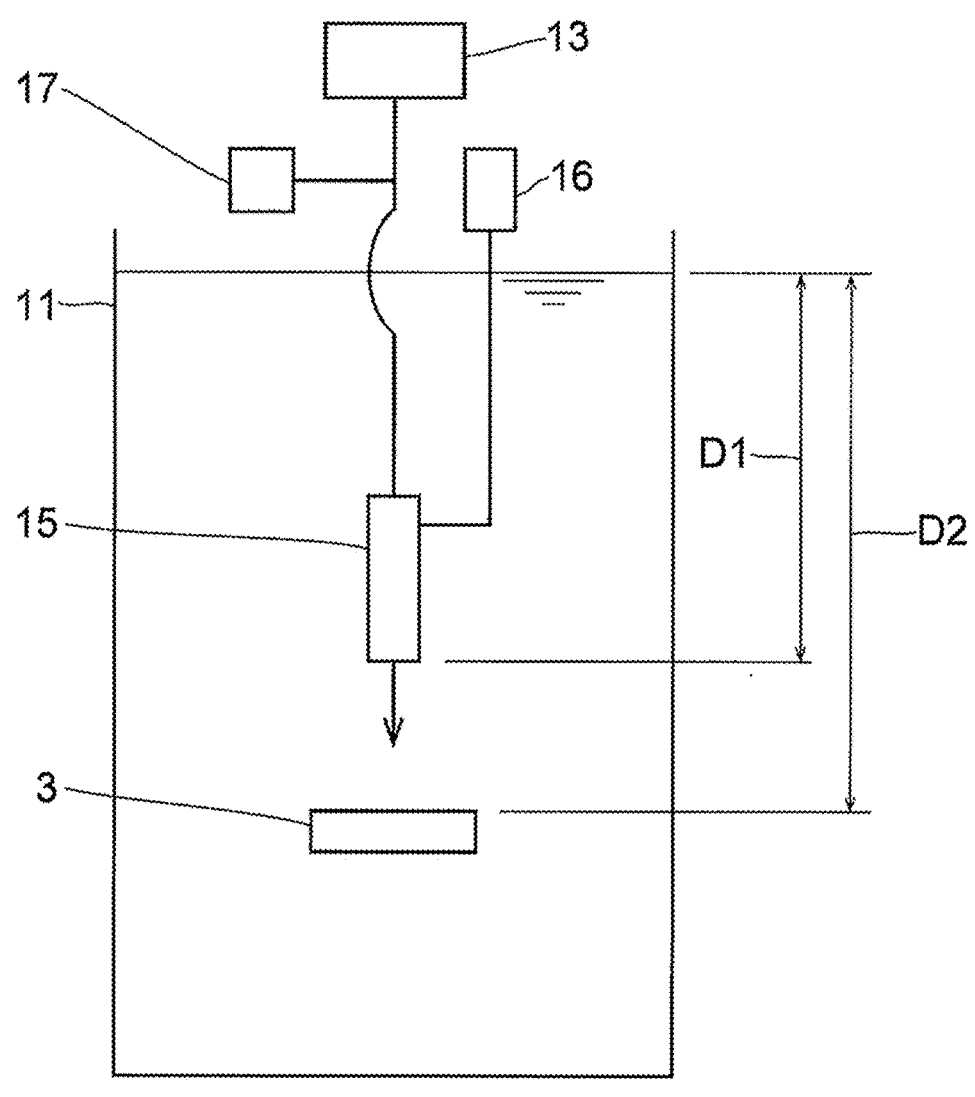
FIG. 3 shows a peening processing machine for the surgical implant according to the embodiment.

FIG. 3 shows a peening processing machine 10 for the surgical implant 3 using a submerged cavitation jet. The peening processing machine 10 includes a processing tank 11, a pump 13, a nozzle 15, a robot (nozzle moving device) 16, and a pressure detector 17.

The processing tank 11 has an opening at an upper side. The processing tank 11 preferably has a depth of the order of 800 mm to 1 m. The processing tank 11 stores processing liquid. The processing liquid is pure water or an aqueous solution containing a rust inhibitor.

The nozzle 15 generates cavitation. The nozzle 15 is disclosed in, for example, JP-A-2006-122834 and JP-A-2014-64979. The nozzle 15 is connected to the pump 13. The nozzle 15 is disposed on the robot 16. At the time of ejection, the nozzle 15 is disposed inside the processing tank 11. For example, the nozzle 15 is positioned downward at a depth D1 from the liquid level. The nozzle depth D1 is, for example, 100 mm to 700 mm.

The robot 16 is, for example, an orthogonal axis robot, a vertical articulated robot, a horizontal articulated robot, or a parallel link robot. The robot 16 freely changes a posture and position of the nozzle 15 relative to the surgical implant 3.

Note that the nozzle 15 maybe fixed, and the robot 16 may change a position and posture of the surgical implant 3.

The pump 13 is a piston pump or a gear pump. The discharge pressure of the pump 13 is, for example, 10 MPa to 70 MPa.

The pressure detector 17 detects a pressure of the processing liquid ejected from the nozzle 15. The ejection pressure is a pressure at the time of ejection.

The surgical implant 3 is placed in the processing tank 11 and immersed in the processing liquid. The distance from the liquid level to the surface of the surgical implant 3 is defined as an immersion depth D2. The immersion depth D2 is, for example, 300 mm to 900 mm.

In step S3, the robot 16 moves the nozzle 15 towards the surgical implant 3. The nozzle 15 then causes the cavitation jet to collide with the surgical implant 3.

When the surgical implant 3 has a low strength or when the target value of the compressive residual stress applied to the surgical implant 3 is small, the cavitation jet may be caused to collide with the vicinity of the surgical implant 3 or the wall surface surrounding the surgical implant 3 without directly colliding with the surgical implant 3.

The jet ejected from the nozzle 15 promotes to generate the cavity. The cavity is a fine bubble that is generated and disappears in a short time due to a pressure difference in a fluid flow. The cavity is introduced around the surgical implant 3 together with the jet. When the cavity disappears, fluid flows rapidly locally and collides with the surface of the surgical implant 3 to perform a peening process. When a peening process is performed by causing the cavitation jet to collide with the surgical implant 3 (hereinafter, cavitation peening), a compressive residual stress is applied to the surface of the surgical implant 3. The compressive residual stress applied to the surgical implant 3 varies depending on the material, but the influence of the shape is small. For example, the compressive residual stress on the surfaces of the surgical implants 3 of pure titanium or titanium alloys are −20 MPa to −200 MPa. The cavitation peening can provide residual stress to deep into the material.

The cavitation jet removes the incomplete penetration area 52*b*. At this time, the spherical portion 521 may break and the base portion 522 may remain. In addition, dimples are formed on the substrate 523 and the base portion 522.

A shot peening process may be performed on an additively manufactured surgical implant 3 (for example, JP-A-2017-520282). For example, when the surgical implant 3 formed of titanium alloy is performed by shot peening process with titanium beads, most of the microscopic surface structures are lost. In this case, the porous body structure may collapse. Further, most of the microscopic spherical structures are lost.

In contrast, when the cavitation peening is performed on the surgical implant 3, most of the microscopic surface structures are maintained. The cavitation peening then provides a large compressive residual stress to the surgical implant 3. The cavitation peening provides a compressive residual stress from the surface of the surgical implant 3 to a depth of the order of 1 mm.

The surgical implant 3 has a complex shape. According to cavitation peening, the cavity floats from the nozzle 15 to the back surface of the surgical implant 3 and to the interior of the surgical implant 3. When the cavity disappears, the surface of the surgical implant 3 is peening processed. Thus, the residual stress is applied to the fine structure on the surface structure of the surgical implant 3 and the back surface of the surgical implant 3 as viewed from the nozzle 15.

According to the present embodiment, the microscopic surface structure of the surgical implant 3 is maintained, thus the hard tissue compatibility is appropriately maintained. In addition, the compressive residual stress is applied to the surface of the surgical implant 3, thus the fatigue strength of the surgical implant is improved.

WORKING EXAMPLE

The surgical implant 3 of Ti-6Al-4V alloy was manufactured by powder bed fusion additive manufacturing. The manufactured surgical implant 3 was subjected to a vacuum heat treatment at a pressure of 2.7 Pa or less (absolute pressure), 800 degrees Celsius, and 2 hours of treatment time. The heat treated surgical implant 3 was subjected to a submerged ejection treatment under the following conditions.

Nozzle: Enlarged nozzle

Processing liquid: 3% dilution of VP-W (trade name, manufactured by Neos Co., Ltd., stock solution components; triethanolamine 3-10%, organic acid amine salts 5-15%, inorganic salts 10-20%, anticorrosive agent 10-20%, water 45-55%)

Immersion depth D1 of the nozzle 15: 450 mm

Immersion depth D2 of the surgical implant 3: 530 mm

Installation direction of the nozzle 15: Vertically downward

Nozzle movement speed: 5 mm/s

Ejection pressure: 50 MPa

Ejection flow rate: 18 L/min

The surface microstructures of artificial intervertebral discs before and after submerged ejection were photographed by scanning electron microscopy (SEM). The SEM was a scanning electron microscopy JCM-5700 manufactured by JEOL Ltd. The surface residual stress of surgical implant before and after submerged ejection was measured by X-ray stress measurement (cos $\alpha$ method). The X-ray stress measuring apparatus was $\mu$-X360s portable X-ray residual stress analyzer manufactured by Pulstec Industrial Co., Ltd. Residual stress was measured at a plurality of specific sites of the surgical implant 3.

Figure 4A:
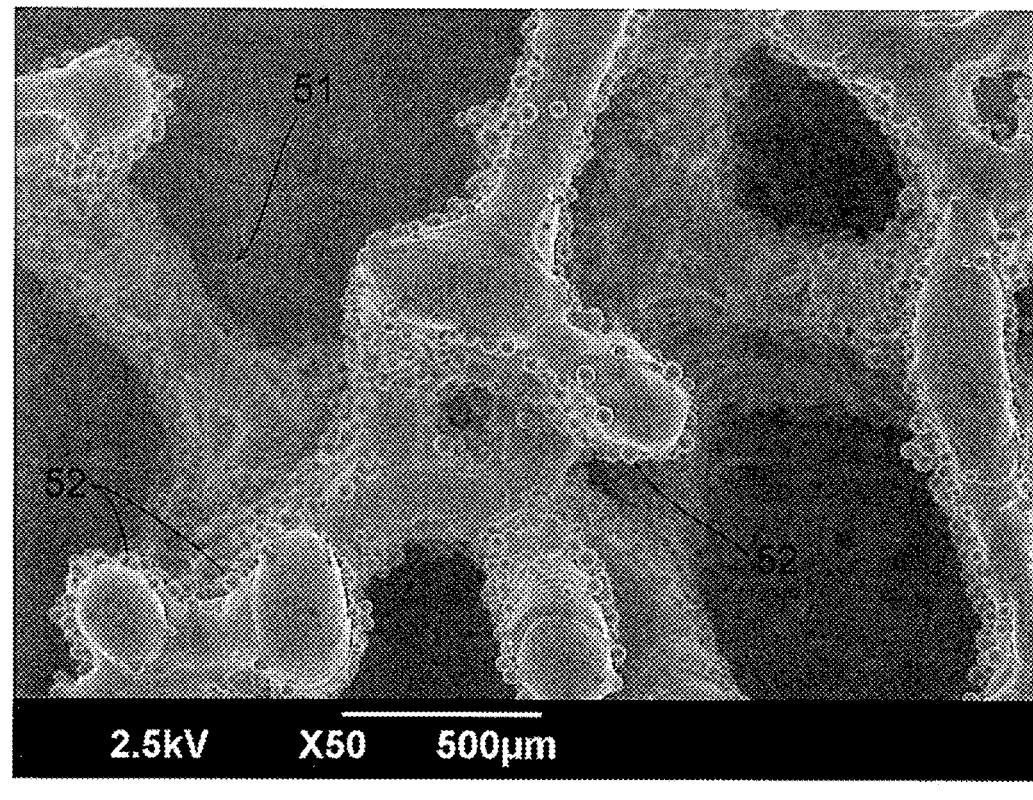
FIG. 4A is a SEM photograph (50×) prior to an ejection treatment of the surgical implant according to the embodiment.
Figure 4B:
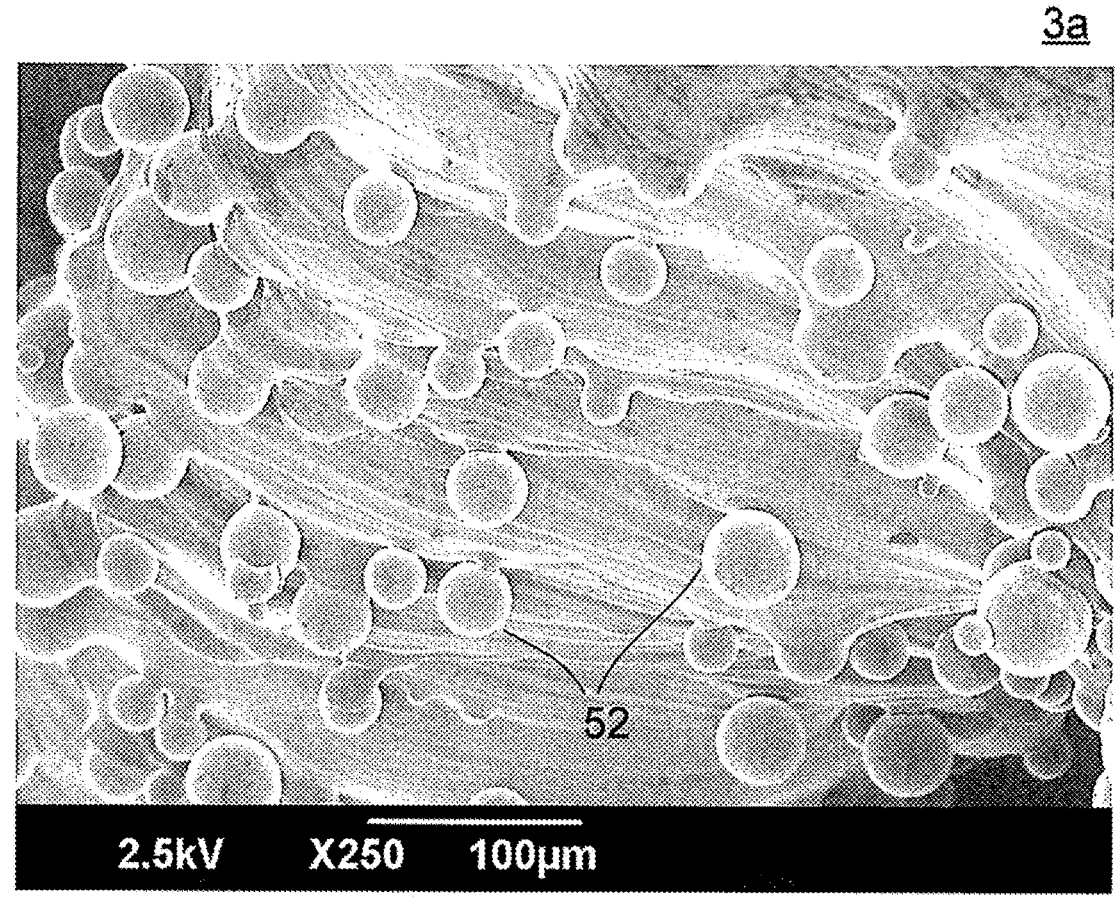
FIG. 4B is a SEM photograph (250×) prior to the ejection treatment of the surgical implant according to the embodiment.

As shown in FIGS. 4A and 4B, the surgical implant 3a prior to submerged ejection has a porous body structure 51 and a microscopic spherical structure 52. The microscopic spherical structure 52 is formed on the surface of the porous body structure 51. The microscopic spherical structure 52 has a complete penetration area 52a and an incomplete penetration area 52b.

Figure 4C:
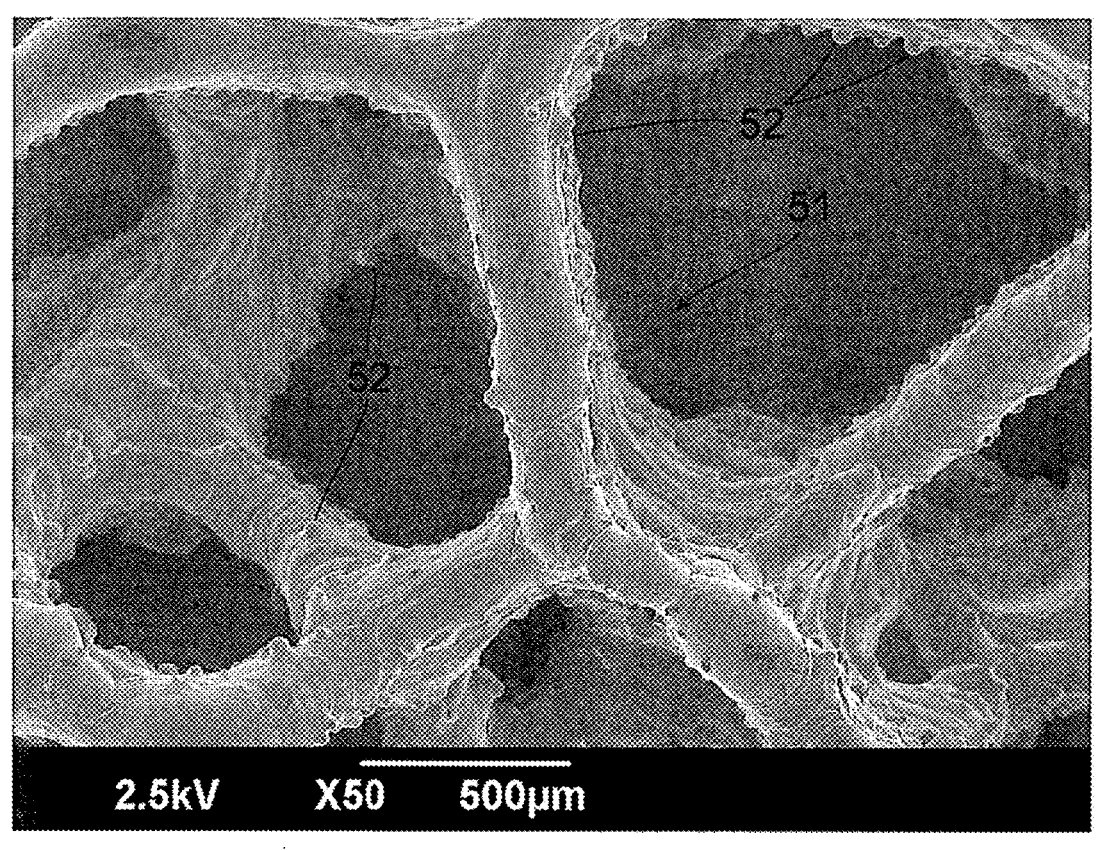
FIG. 4C is a SEM photograph (50×) after the ejection process of the surgical implant according to the embodiment.
Figure 4D:
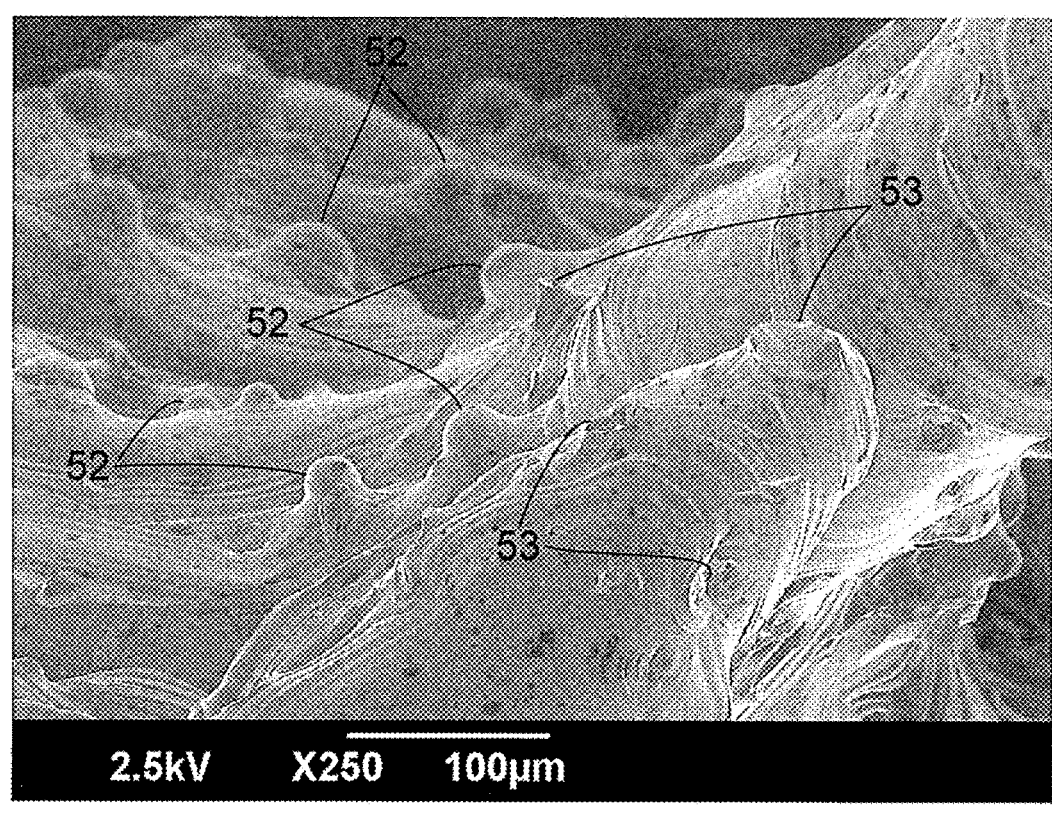
FIG. 4D is a SEM photograph (250×) after the ejection process of the surgical implant according to the embodiment.

As shown in FIGS. 4C and 4D, the surgical implant 3b after submerged ejection has a porous body structure 51, a microscopic spherical structure 52, and a dimple 53. By the submerged ejection process, the structure of the porous body structure 51 was maintained without collapsing the porous body structure 51. In the present working example, the structure of the porous body structure 51 was completely maintained. The dimples 53 appeared on the surface of the surgical implant 3b. The dimple 53 is a fracture mark from which the incomplete penetration area 52b has been removed.

The diameter of the base portion 522 of the microscopic spherical structure 52 remaining on the surgical implant 3b after submerged ejection was greater than or equal to about 70% of the diameter of the spherical portion 521.

The surface stress of the surgical implant 3a prior to cavitation jet processing was 42 MPa. Before the cavitation jet processing, a tensile stress (positive value) was given by additive manufacturing.

The surface stress of the surgical implant 3b after cavitation jet processing was −141 MPa. It was confirmed that the compressive stress (negative value) was given by the peening effect due to the cavitation jet.

The present invention is not limited to the above-described embodiments, and various modifications can be made without departing from the gist of the present invention, and all technical matters included in the technical idea described in the claims are the subject of the present invention. While the above embodiments have been shown by way of example, those skilled in the art will recognize that various alternatives, modifications, variations, and improvements can be made from the disclosure herein, which fall within the scope of the appended claims.

REFERENCE SIGNS LIST

3, 3a, 3b Surgical implant
15 Nozzle
51 Porous body structure
52 Microscopic spherical structure
52b Incomplete penetration area
53 Dimple

What is claimed is:

1. A surface treatment method for a surgical implant, the method comprising:

placing an additive manufactured surgical implant in a processing liquid, the surgical implant including a microscopic spherical structure having a complete penetration area and an incomplete penetration area, the microscopic spherical structure including
a spherical portion,
a substrate, and
a base portion connecting the spherical portion and the substrate; and causing a nozzle immersed in the processing liquid to eject a cavitation jet of the processing liquid to the surgical implant to remove the incomplete penetration area remaining on a surface of the surgical implant while maintaining the structure of the complete penetration area and apply a compressive residual stress to the surface of the surgical implant.

2. The surface treatment method for the surgical implant according to claim 1, wherein the base portion in the incomplete penetration area has a dimension equal to or smaller than 70% of a diameter of the spherical portion.

3. The surface treatment method for the surgical implant according to claim 1, wherein the surgical implant is formed of bioinert metal.

4. The surface treatment method for the surgical implant according to claim 3, wherein the bioinert metal is pure titanium, or titanium alloy.

5. The surface treatment method for the surgical implant according to claim 1, wherein the nozzle ejects the processing liquid at a pressure of 50 MPa to 70 MPa.

6. The surface treatment method for the surgical implant according to claim 2, wherein the surgical implant is formed of bioinert metal.

7. The surface treatment method for the surgical implant according to claim 2, wherein the nozzle ejects the processing liquid at a pressure of 50 MPa to 70 MPa.

8. The surface treatment method for the surgical implant according to claim 1, wherein the placing the additive manufactured surgical implant in the processing liquid includes placing the additive manufactured surgical implant in an immersion depth of 300 mm to 900 mm, the immersion depth being a distance from a processing liquid level to a surface of the additive manufactured surgical implant.

9. The surface treatment method for the surgical implant according to claim 1, wherein the compressive residual stress measured by X-ray stress measurement (cos $\alpha$ method) is −20 MPa to −200 MPa.

10. The surface treatment method for the surgical implant according to claim 1, wherein the residual stress is applied on the surface of the surgical implant and a back surface of the surgical implant as viewed from the nozzle.

* * * * *